United States Patent

Krüger et al.

[11] Patent Number: 5,164,383
[45] Date of Patent: Nov. 17, 1992

[54] O-HALOGENOCYCLOPENTYL S-ALKYL (DI)THIOPHOSPHORIC-(PHOSPHONIC) ESTER DERIVATIVES, PROCESSES FOR THEIR PREPARATION, AND THEIR USE AS PESTICIDES

[75] Inventors: Bernd-Wieland Krüger, Bergisch Gladbach; Michael Negele, Köln; Jürgen Hartwig, Leverkusen; Christoph Erdelen, Leichlingen, Fed. Rep. of Germany; Wilhelm Stendel, Wuppertal, all of Fed. Rep. of Germany

[73] Assignee: Bayer Aktiengesellschaft, Leverkusen, Fed. Rep. of Germany

[21] Appl. No.: 854,182

[22] Filed: Mar. 20, 1992

[30] Foreign Application Priority Data

Mar. 30, 1991 [DE] Fed. Rep. of Germany ....... 4110486

[51] Int. Cl.⁵ .................. A01N 57/04; C07F 9/40; C07F 9/24; C07F 9/177
[52] U.S. Cl. .................... 514/120; 514/129; 514/137; 514/141; 514/144; 558/178; 558/185; 558/199; 558/202; 558/204
[58] Field of Search ............ 558/178, 199, 202, 204; 514/120, 137, 141, 144

[56] References Cited

U.S. PATENT DOCUMENTS 4,973,583 11/1990 Krüger et al. .................. 514/141

*Primary Examiner*—Mary C. Lee
*Assistant Examiner*—Michael G. Ambrose
*Attorney, Agent, or Firm*—Sprung Horn Kramer & Woods

[57] ABSTRACT

O-Halogenocyclopentyl S-alkyl (di)thiphosphoric(-phosphonic) acid ester derivatives of the general formula (I)

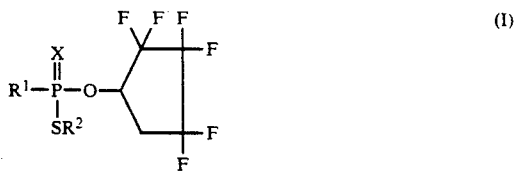

in which $R^1$ represents alkyl, alkoxy or the radical

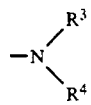

$R^3$ represents hydrogen or alkyl and
$R^4$ represents hydrogen, alkyl, —COH (formyl) or optionally halogen-substituted —CO-alkyl (acyl),
$R^2$ represents alkyl or alkoxyalkyl and
X represents oxygen or sulphur, can be used as pesticides.

8 Claims, No Drawings

O-HALOGENOCYCLOPENTYL S-ALKYL (DI)THIOPHOSPHORIC-(PHOSPHONIC) ESTER DERIVATIVES, PROCESSES FOR THEIR PREPARATION, AND THEIR USE AS PESTICIDES

The invention relates to new O-halogenocyclopentyl S-alkyl (di)thiophosphoric(phosphonic) ester derivatives, to a plurality of processes for their preparation, and to their use as pesticides, in particular as insecticides, acaricides and nematicides.

It has already been disclosed that certain O-halogenocyclobutyl S-(alkyl) (di)thiophosphoric esters such as, for example, S-propyl O-ethyl O-(3,3,2-trifluoro-2-chloro-cyclobutyl)thiophosphate can be used for combating pests (cf. U.S. Pat. No. 4,973,583).

However, the insecticidal, acaricidal and nematicidal action of the known compounds is not always entirely satisfactory in all fields of application, in particular when low concentrations and low amounts of active compound are applied.

New O-halogenocyclopentyl S-alkyl (di)thiophosphoric(phosphonic) acid ester derivatives of the general formula (I)

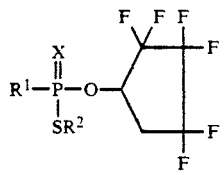
(I)

have now been found, in which
$R^1$ represents alkyl, alkoxy or the radical

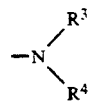

where
$R^3$ represents hydrogen or alkyl and
$R^4$ represents hydrogen, alkyl, —COH (formyl) or optionally halogen-substituted —CO—alkyl (acyl),
$R^2$ represents alkyl or alkoxyalkyl and
X represents oxygen or sulphur.

The compounds of the formula (I) may have one or more centres of asymmetry. They can therefore exist in various forms of isomers, which can be obtained in various ratios. The invention relates to the mixtures of isomers as well as to the individual isomers.

For simplicity's sake, the following text will, however, always mention compounds of the formula (I) even though this is intended to mean the pure compounds as well as, if appropriate, the mixtures which have various proportions of isomeric compounds.

Furthermore, it has been found that the new O-halogenocyclopentyl S-alkyl (di)thiophosphoric(phosphonic) acid ester derivatives of the general formula (I) are obtained when a) halogenothio- or halogenodithiophosphates of the formula (II)

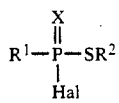
(II)

in which
$R^1$, $R^2$ and X have the abovementioned meaning and Hal represents halogen,
are reacted with cyclopentanol derivatives of the formula (III)

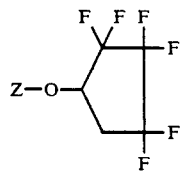
(III)

in which Z represents hydrogen or an equivalent of an alkali metal ion, if appropriate in the presence of diluents and if appropriate in the presence of bases, or when b) to prepare compounds of the formula (I) in which $R^1$ represents alkoxy or —$NR^3R^4$, acid halides of the formula (IV)

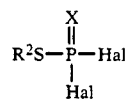
(IV)

in which X, $R^2$ and Hal have the abovementioned meaning, are reacted, in a first reaction step, with compounds of the formula

(V)

in which $R^5$ represents alkoxy or the radical —$NR^3R^4$, where $R^3$ and $R^4$ have the abovementioned meaning, if appropriate in the presence of solvents and if appropriate in the presence of bases, and the resulting product of the formula (VI)

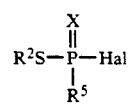
(VI)

in which X, $R^2$, $R^5$ and Hal have the abovementioned meaning, is subsequently reacted, in a second reaction step, with compounds of the formula (III), if appropriate in the presence of diluents and if appropriate in the presence of bases, or when c) in a first reaction step, compounds of the formula (VII)

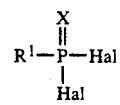
(VII)

in which $R^1$, X and Hal have the abovementioned meaning, are reacted with compounds of the formula (III), if appropriate in the presence of diluents and if appropriate in the presence of bases, and the resulting compounds of the formula (VIII)

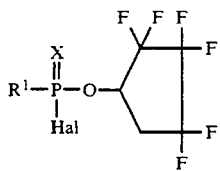
(VIII)

in which $R^1$, X and Hal have the abovementioned meaning, are reacted, in a second reaction step, with compounds of the formulae (IXa) or (IXb)

 (IXa)

or

 (IXb)

in which $Z^1$ represents an equivalent of an alkali metal ion, if appropriate in the presence of a diluent, and the resulting compounds of the formula (X)

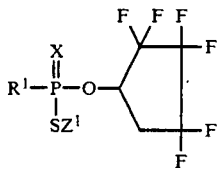
(X)

in which $R^1$, X and $Z^1$ have the abovementioned meaning, are reacted with compounds of the formula (XI)

 (XI)

in which $R^2$ and Hal have the abovementioned meaning, if appropriate in the presence of a diluent and if appropriate in the presence of a base, or when d) to prepare compounds of the formula (I) in which $R^1$ represents alkyl and X represents sulphur, compounds of the formula (XII)

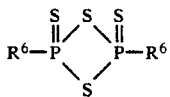
(XII)

in which $R^6$ represents alkyl, are reacted, in a first reaction step, with cyclopentanol derivatives of the formula (III), if appropriate in the presence of diluents and if appropriate in the presence of bases, and the resulting compounds of the formula (XIII)

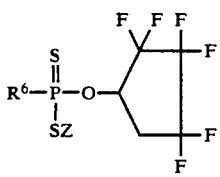
(XIII)

in which $R^6$ and Z have the abovementioned meaning, are reacted, in a second step, with compounds of the formula (XI), if appropriate in the presence of diluents and if appropriate in the presence of bases, or when e) to prepare compounds of the formula (I) in which $R^1$ represents $-NR^3R^4$, compounds of the formula (IV) are reacted, in a first step, with compounds of the formula (III), if appropriate in the presence of diluents and if appropriate in the presence of bases, and the resulting compounds of the formula (XIV)

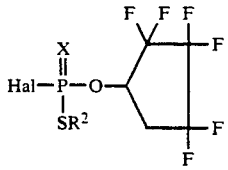
(XIV)

in which X, $R^2$ and Hal have the abovementioned meaning, are reacted, in a second step, with compounds of the formula (XV)

(XV)

in which $R^3$ and $R^4$ have the abovementioned meaning, if appropriate in the presence of a diluent and if appropriate in the presence of a base, or when f) to prepare compounds of the formula (I) in which $R^4$ represents formyl or acyl, compounds of the formula (XVI)

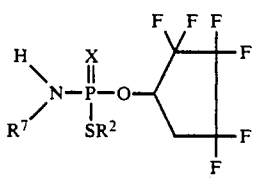
(XVI)

in which
X and $R^2$ have the abovementioned meaning and
$R^7$ represents hydrogen or alkyl,
are reacted with compounds of the formula (XVII)

 (XVII)

in which
$R^8$ represents hydrogen or optionally halogen-substituted alkyl and
Y represents halogen or another group which is eliminated in acylation reactions,
if appropriate in the presence of a diluent or if appropriate in the presence of a base.

Furthermore, it has been found that the new compounds of the general formula (I) are highly pesticidally active, in particular against undesirable arthropods, such as insects and spider mites, and also against nematodes. The new compounds are therefore a valuable enrichment of the art.

In the general formulae, the radical

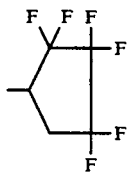

denotes the 2,2,3,3,4,4-hexafluorocyclopentyl radical of the formula

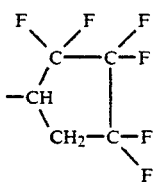

The radicals mentioned in the general formulae are illustrated as follows:

Alkyl denotes straight-chain or branched alkyl having preferably 1 to 6, particularly preferably 1 to 4, and very particularly preferably 1 to 3, carbon atoms, mention being made specifically of methyl, ethyl, n- and i-propyl as well as n-, i-, sec- and t-butyl.

The explanations given in the case of alkyl apply to the alkyl moieties of —CO-alkyl, alkoxy and alkoxyalkyl. Of the CO—alkyl radicals, —CO—$C_1$-$C_4$-alkyl and, in particular, —COCH$_3$ and —COC$_2$H$_5$ must be emphasised specifically. Alkoxy radicals which must be emphasised specifically are $C_1$-$C_3$-alkoxy, in particular methoxy and ethoxy. Alkoxyalkyl radicals which should be emphasised specifically are $C_1$-$C_4$-alkoxy-$C_1$-$C_2$-alkyl, in particular methoxymethyl, ethoxymethyl, methoxyethyl and ethoxyethyl.

Halogen-substituted CO-alkyl contains one or more, preferably 1 to 5, particularly preferably 1 to 3, identical or different halogen atoms, where, in particular, COCF$_3$ must be emphasised specifically. This also applies correspondingly to the alkyl radical $R^8$.

Halogen denotes fluorine, chlorine, bromine and iodine, preferably chlorine, bromine and iodine, particularly preferably chlorine and bromine, and very particularly preferably chlorine. In halogen-substituted —CO-alkyl, halogen preferably denotes fluorine, chlorine and/or bromine, particularly preferably fluorine and/or chlorine, and very particularly preferably fluorine.

Lithium, sodium and potassium ions are preferred as alkali metal ions.

$R^1$ preferably represents $C_1$-$C_6$-alkyl, $C_1$-$C_6$-alkoxy or —NR$^3$R$^4$ where $R^3$ represents hydrogen or $C_1$-$C_6$-alkyl and $R^4$ represents hydrogen, $C_1$-$C_6$-alkyl, HCO— (formyl) or optionally halogen-substituted —CO—C$_1$-$C_4$-alkyl (acyl).

$R^2$ preferably represents $C_1$-$C_6$-alkyl or $C_1$-$C_6$-alkoxy-$C_1$-$C_6$-alkyl.

Preferred according to the invention are the compounds of the formula (I) in which there is a combination of these meanings mentioned above as preferred.

$R^1$ particularly preferably represents $C_1$-$C_4$-alkyl, $C_1$-$C_4$-alkoxy or —NR$^3$R$^4$ where $R^3$ represents hydrogen or $C_1$-$C_4$-alkyl and $R^4$ represents hydrogen, $C_1$-$C_4$-alkyl, HCO— or optionally halogen-substituted —CO—$C_1$-$C_4$-alkyl.

$R^2$ particularly preferably represents $C_1$-$C_4$-alkyl or $C_1$-$C_4$-alkoxy-$C_1$-$C_4$-alkyl.

Particularly preferred according to the invention are the compounds of the formula (I) in which there is a combination of these meanings mentioned above as particularly preferred.

$R^1$ very particularly preferably represents $C_1$-$C_3$-alkyl, methoxy, ethoxy, —NHCH$_3$ or —NHC$_2$H$_5$.

$R^2$ very particularly preferably represents $C_3$-$C_4$-alkyl (in particular n- and i-propyl, n-butyl, i-butyl or sec-butyl).

Very particularly preferred according to the invention are the compounds of the formula (I) in which there is a combination of these meanings mentioned above as very particularly preferred.

The compounds of the formula (I) in which X represents oxygen are particularly emphasised according to the invention.

The abovementioned general definitions of the radicals or explanations, or the definitions of the radicals or explanations which have been mentioned in ranges of preference, can be combined with each other as desired, that is to say also between the particular ranges of preference. The same applies correspondingly to the precursors and intermediates.

The following O-halogenocyclopentyl S-alkyl (di)-thiophosphoric(phosphonic) acid ester derivatives of the general formula (I) may be mentioned specifically by way of example in addition to those compounds which are mentioned in the preparation examples:

| $R^1$ | $R^2$ | X |
|---|---|---|
| (C$_2$H$_5$)$_2$N | —C$_3$H$_7$-n | O |
| (CH$_3$)$_2$N | —C$_3$H$_7$-n | O |
| CH$_3$O | —C$_3$H$_7$-n | O |
| CH$_3$O | —CH—C$_2$H$_5$<br>    \|<br>    CH$_3$ | O |
| CH$_3$O | —C$_3$H$_7$-n | S |
| CH$_3$O | —CH—C$_2$H$_5$<br>    \|<br>    CH$_3$ | S |
| CH$_3$NH | —C$_3$H$_7$-n | O |
| CH$_3$NH | —CH—C$_2$H$_5$<br>    \|<br>    CH$_3$ | O |
| C$_2$H$_5$NH | —CH—C$_2$H$_5$<br>    \|<br>    CH$_3$ | O |
| C$_2$H$_5$NH | —C$_3$H$_7$-n | S |
| C$_2$H$_5$NH | —CH—C$_2$H$_5$<br>    \|<br>    CH$_3$ | S |

The phosphoric(phosphonic) acid derivatives of the general formula (II), (IV), (VII) and (XII) which are used as starting substances are known or can be prepared by known methods (cf. "Methoden der organischen Chemie" [Methods in Organic Chemistry] (Houben-Weyl) Vol. E2, 1982, Georg Thieme Verlag Stuttgart, N.Y., p. 300 et seq. and p. 487 et seq.).

The starting substances of the formulae (VIII), (X), (XIII) and (XIV) are new and part of the present invention. They are obtained in the course of process variants c), d) and e). They are isolated and purified by the customary methods, for example by distillation or chromatography.

The new compounds of the formulae (VIII), (X) and (XIV) can be combined in the following formula (XVIII)

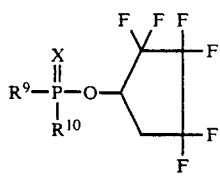

in which (a) $R^9$ has the meaning of $R^1$ and $R^{10}$ represents halogen or $SZ^1$ or (b) $R^9$ represents halogen and $R^{10}$ represents $SR^2$, where $R^1$, $Z^1$ and $R^2$ have the abovementioned meaning.

The cyclopentyl derivatives of the formula (III) which are used as starting substances in the processes according to the invention are new. They can be obtained by known methods. For example, the compound of the formula (III) in which Z represents hydrogen can be prepared by an addition reaction of phenol or 1-propanol with hexafluorodichlorocyclopentene, hydrogenating the product and subsequently carrying out an ether cleavage according to the following equation:

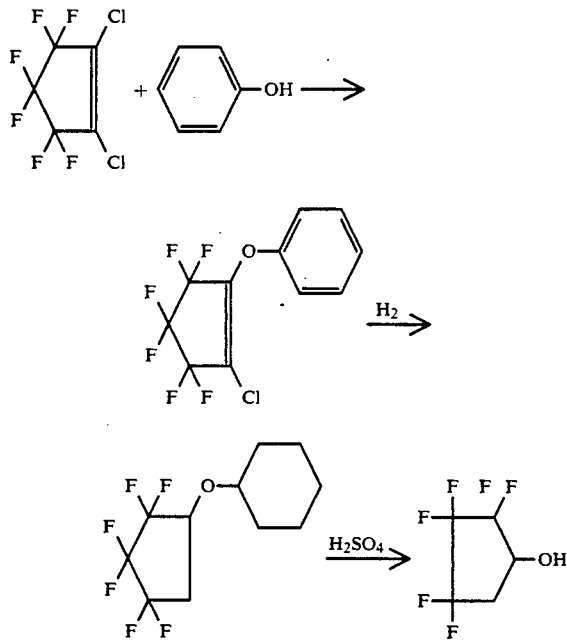

The alkali metal salts can be obtained from the alcohol by the customary methods.

The remaining compounds to be used as starting substances are know or can be prepared by generally known methods.

Diluents which are suitable for process variant a) according to the invention are virtually all inert organic diluents and their mixtures. These include, in particular, aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methylpyrrolidone, and also dimethyl sulphoxide, tetramethylene sulphone and hexamethylphosphoric triamide.

For carrying out process variant a) according to the invention, 1 to 2 mol, preferably 1.0 to 1.8 mol, of cyclopentyl compound of the formula (III) are employed per mole of phosphorus derivative of the formula (II).

Diluents which can be used for process variants b), c), d), e) and f) according to the invention are virtually all inert organic diluents. Those diluents which have been mentioned in connection with the description of process variant a) according to the invention are preferably used.

If appropriate, process variants a), b), c), d), e) and f) can be carried out in the presence of bases. Bases which can be used are all customary bases. The following are particularly preferred: alkali metal carbonates and alkali metal alcoholates such as sodium carbonate and potassium carbonate, sodium methylate, potassium methylate, sodium ethylate and potassium ethylate, furthermore aliphatic, aromatic or heterocyclic amines, for example collidine, triethylamine, trimethylamine, dimethylaniline, dimethylbenzylamine, tetraethylenediamine (DABCO) and pyridine. It is preferred to add the bases in such an amount as is necessary for scavenging the hydrogen halide formed.

Process variants a), b), c), d), e) and f) according to the invention are generally carried out at temperatures between $-70°$ C. and $+150°$ C. The range between $-40°$ C. and $110°$ C. is preferred.

The reactions are generally carried out under atmospheric pressure.

For carrying out process variant b) according to the invention, 1 to 1.6 mol, preferably 1 to 1.4 mol, of the compound of the formula (V) and 1 to 2, preferably 1 to 1.8, mol of the cyclopentyl compound of the formula (III) are employed per mole of the compound of the formula (IV).

For carrying out process variant c) according to the invention, 1 to 1.6 mol, preferably 1 to 1.4 mol, of the cyclopentyl compound of the formula (III), 1 to 2, preferably 1 to 1.8, mol of the compounds of the formulae (IXa) or (IXb) and 1 to 2, preferably 1 to 1.8, mol of the alkyl halides of the formula (XI) are employed per mole of the compound of the formula (VII).

For carrying out process variant d), 2 to 3 mol, preferably 2 to 2.5 mol, of the cyclopentyl compound of the formula (III) and 2 to 3, preferably 2 to 2.5, mol of the alkyl halides of the formula (XI) are employed per mole of the compound of the formula (XII).

For carrying out process variant e) according to the invention, 1 to 2 mol, preferably 1 to 1.3 mol, of the cyclopentyl compound of the formula (III) are employed per mole of the compound of the formula (IV), and, for the second reaction step, 1 to 4 mol, preferably 1 to 1.5 mol, of the amine of the formula (XV) are employed per mole of the monohalide of the formula (XIV).

To obtain the compounds of the formula (I) in which $R^1$ represents acyl- or formylamino, 1 to 2, preferably 1 to 1.3, mol of the compound of the formula (XVII) are employed in process variant f) per mole of the phosphorus compound of the formula (XVI). In addition to carboxylic acid halides, preferably the chlorides, other carboxylic acid derivatives such as carboxylic anhydrides, for example acetic anhydride, are also employed advantageously in process variant f).

Working-up of the compounds according to the invention is carried out by customary methods. Some of the new compounds are obtained in the form of oils, some of which cannot be distilled without undergoing decomposition, but are freed from the last volatile components by so-called "incipient distillation", that is to say by prolonged heating under reduced pressure to moderately elevated temperatures, and are purified in this manner. The refractive index can be used to characterise them.

The active compounds according to the invention are suitable for combating animal pests, in particular insects, arachnida and nematodes, encountered in agriculture, in forests, in the protection of stored products and of materials, and in the hygiene field, and have good plant tolerance and favourable toxicity to warm-blooded animals. They are active against normally sensitive and resistant species and against all or some stages of development. The abovementioned pests include:

From the order of the Isopoda, for example *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera spec.*

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Phylloxera vastatrix,* Pemphigus spp., *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharanois* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The phytoparasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp. and Trichodorus spp.

The active compounds of the formula (I) according to the invention are distinguished by a high insecticidal, acaricidal and, above all, nematicidal activity. They can be employed in particular against insects which are harmful to plants, such as, for example, against the caterpillars of the cabbage moth (*Plutella maculipennis*) or against the larvae of the mustard beetles (*Phaedon cochleariae*) and against mites which are harmful to plants, such as, for example, against the greenhouse red spider mite (*Tetranychus urticae*). In addition, they are outstandingly suitable for combating soil-dwelling insects and nematodes and can be employed, for example, for combating *Phorbia antiqua* grubs or nematodes of the genus *Meloidogyne incognita.* A good root-systemic action, for example against *Phaedon cochleariae* larvae, must also be emphasised. The nematicidal action of the active compounds according to the invention has also been proved in the in-vitro test, for example against nematodes of the genus *Caenorhabditis elegans*, which live as endoparasites.

In addition, the active compounds of the formula (I) according to the invention have a high activity against hygiene pests and stored product pests and can be employed, for example, for combating the oriental cockroach (*Blatta orientalis*) or for combating the grain weevil (*Sitophilus granarius*). In addition, the active compounds according to the invention can be particularly successfully used for combating pests which live parasitically on warm-blooded species, (both ecto- and endoparasites), such as, for example, against the larvae of the sheep maggot fly (*Lucilia cuprina*), against cattle ticks (*Boophilus microplus*), against seal mites (*Psoroptes ovis*), against stable flies (*Stomoxys calcitrans*) or against autumn flies (*Musca autumnalis*).

Besides this, the active compounds of the formula (I) according to the invention also have a good fungicidal activity and can be employed for combating plant diseases such as, for example, against the pathogen causing rice blast disease (*Pyricularia oryzal*) or against scab and *Botrytis pathogens*.

When applied in appropriate amounts, the active compounds of the formula (I) according to the invention also show a herbicidal activity.

The active compounds according to the invention can be converted to the customary formulations, such as solutions, emulsions, suspensions, powders, foams, pastes, granules, aerosols, natural and synthetic materials impregnated with active compound, very fine capsules in polymeric substances and in coating compositions for seed, furthermore in formulations used with burning equipment, such as fumigating cartridges, fumigating cans, fumigating coils and the like, as well as ULV cold mist and warm mist formulations.

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, furthermore in formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is liquid solvents, liquefied gases under pressure, and/or solid carriers, optionally with the use of surface-active agents, that is emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkysulphonates, alkyl sulphates, arylsulphonates as well as albumen hydrolysis products; as dispersing agents there are suitable: for example lignin-sulphite waste liquors and methycellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in their commercially available formulations and in the use forms, prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

The compounds according to the invention are also especially suitable for treating generative or vegetative propagation material (seed), such as cereals, maize, potatoes, onions etc. The application rates are preferably 0.5 to 20, in particular 1 to 5, g per kg of propagation material.

When used against hygiene pests and pests of stored products, the active compounds are distinguished by an excellent residual action on wood and clay as well as by a good stability to alkali on limed substrates.

The active compounds according to the invention are also suitable for combating insects, mites, ticks etc. in the sectors of animal keeping and cattle breeding; better results, for example higher milk production, greater weight, more attractive animal pelt, longer life etc., can be achieved by combating the pests.

The application of the active compounds according to the invention occurs in this sector in a known fashion, such as by external application in the form of, for example, dipping, spraying, pouring-on, spotting-on and dusting.

The preparation of the compounds according to the invention will be explained with reference to the examples below.

EXAMPLE 1

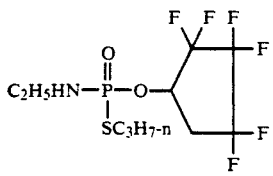

10 g (0.05 mol) of S-propyl dichlorothiophosphate are dissolved in 500 ml of hexane and to the solution there are first added, between 0° and −5° C., 10 ml (0.07 mol) of triethylamine, and then 10 g (0.052 mol) of 2,2,3,3,4,4-hexafluorocyclopentan-1-ol, dissolved in 25 ml of methylene chloride. The mixture is stirred for 2 hours at 20° C. and 5 g (0.11 mol) of ethylamine are then added dropwise to the reaction mixture at 20° C. To complete the reaction, the mixture is stirred for 24 hours at 20° C., the solid is filtered off, and the solvent is distilled off under reduced pressure. The residue is then purified further by filtration through silica gel (cyclohexane:ethyl acetate=7:3 parts by volume). After the solvent has been distilled off, 8.5 g (47% of theory) of O-(2,2,3,3,4,4-hexafluorocyclopentyl) S-propyl N-ethylthiophosphoramide of refractive index $n_D^{20}=1.4292$ are obtained.

EXAMPLE 2

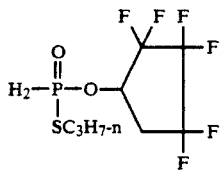

20 g (0.1 mol) of S-propyl dichlorothiophosphate are dissolved in 500 ml of hexane, and the solution is first treated, between 0° and −5° C., with 20 ml (0.14 mol) of triethylamine and then with 20 g (0.1 mol) of 2,2,3,3,4,4-hexafluorocyclopentan-1-ol, dissolved in 50 ml of methylene chloride. The mixture is stirred for 2 hours at 20° C., and ammonia is then passed in at 20° C. (DC check). To complete the reaction, the mixture is stirred for 24 hours at 20° C., the solid is filtered off, and the solvent is distilled off under reduced pressure. The residue is then purified further by filtration through silica gel (cyclohexane:ethyl acetate=7:3 parts by volume). After the solvent has been distilled off, 8.6 g (27% of theory) of O-(2,2,3,3,4,4-hexafluorocyclopentyl) S-propyl thiophosphoramidate of refractive index $n_D^{20}=1.4390$ are obtained.

EXAMPLE 3

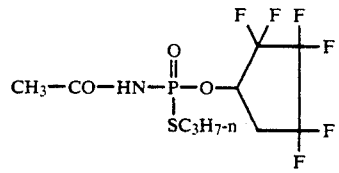

3.2 g (0.01 mol) of O-(2,2,3,3,4,4-hexafluorocyclopentyl) S-propyl thiophosphoramidate are dissolved in 50 ml of pyridine and, at 20° C., the solution is treated with 0.5 g of 4-pyrrolidinopyridine and 1 g of acetic anhydride (0.011 mol). The mixture is stirred for 24 hours at 40° C., and the pyridine is then distilled off under reduced pressure, and the residue is filtered off through silica gel (cyclohexane:ethyl acetate=7:3 parts by volume). After the solvent has been distilled off, 1.1 g (29% of theory) of O-(2,2,3,3,4,4-hexafluorocyclopentyl) S-propyl thiophosphoracet amidate of refractive index $n_D^{20}=1.4751$ are obtained.

EXAMPLE 4

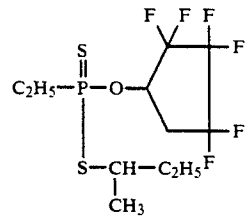

6.3 g (0.02 mol) of ethanethiophosphonic dithioanhydride are suspended in toluene and, at 20° C., the suspension is treated with 7.8 g (0.04 mol) of 2,2,3,3,4,4-hexafluorocyclopentan-1-ol, dissolved in 10 ml of toluene. The mixture is stirred for 0.5 hours at 20° C., 8 ml (0.058 mol) of triethylamine are then added dropwise to the reaction mixture at 20° C. (exothermal reaction, up to approx. 40° C.). Stirring is continued at 50° C. for another 2 hours, and 9.1 g (0.066 mol) of sec.-butyl bromide are then added at 20° C. To complete the reaction, the mixture is stirred for 24 hours at 80° C., the reaction mixture is then poured into water and extracted with methylene chloride, the extract is dried with magnesium sulphate and filtered, and the solvent is distilled off under reduced pressure. The residue is then purified further by filtration through silica gel (cyclohexane:ethyl acetate=7:3 parts by volume). After the solvent has been distilled off, 9.4 g (63% of theory) of O-(2,2,3,3,4,4-hexafluorocyclopentyl S-(1-methylpropyl) ethanethiophosphate of refractive index $n_D^{20}=1.4575$ are obtained.

EXAMPLE 5

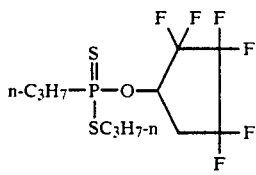

O-(2,2,3,3,4,4-Hexafluorocyclopentyl) S-propyl propanethiophosphonate of refractive index $n_D^{20} = 1.4595$ is obtained analogously to Example 4.

EXAMPLE 6

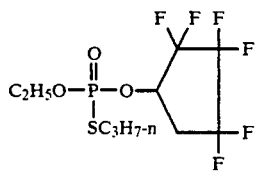

4 g (0.02 mol) of 2,2,3,3,4,4-hexafluorocyclopentan-1-ol, dissolved in 50 ml of tetrahydrofuran, are treated, at −70° C., with 8 ml of a 2.5-molar butyllithium solution in hexane. The mixture is heated to −20° C. and 5 g (0.02 mol) of O-ethyl S-propyl chlorothiophosphate are then added dropwise. To complete the reaction, the mixture is stirred for 24 hours at 20° C., a little water is added to the reaction mixture, and the mixture is filtered through silica gel. After the solvent has been distilled off and the residue has been distilled, 1.6 g (22% of theory) of O-ethyl O-(2,2,3,3,4,4-hexafluorocyclopentyl) S-propyl thiophosphate of a boiling point of b.p.$_{0.15}$ 90°–92° C. are obtained.

EXAMPLE 7

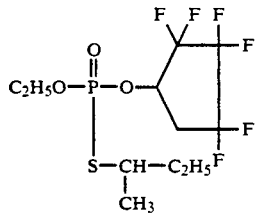

10.5 g (0.05 mol) of S-(1-methyl-propyl) thiophosphate are dissolved in 200 ml of hexane and first treated, between 0° and −5° C., with 10 ml (0.07 mol) of triethylamine and then with 2.3 g (0.05 mol) of ethanol, dissolved in 25 ml of hexane. The mixture is stirred for 2 hours at 20° C. and then, at 20° C., first 10 ml (0.07 mol) of triethylamine and then 10 g (0.052 mol) of 2,2,3,4,4-hexafluorocyclopentan-1-ol are added dropwise to the reaction mixture. To complete the reaction, the mixture is stirred for 24 hours at 20° C., the solid is filtered off, and the solvent is distilled off under reduced pressure. The residue is then purified further by filtration through silica gel (cyclohexane:ethyl acetate=7:3 parts by volume). After the solvent has been distilled off, 18.0 g (98% of theory) of O-(2,2,3,3,4,4-hexafluorocyclopentyl) S-propyl N-ethylthiophosphoramidate of refractive index $n_D^{20} = 1.4265$ are obtained.

The following were prepared analogously:

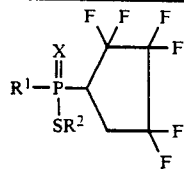

| Ex. No. | R$^1$ | R$^2$ | X | Physical data |
|---|---|---|---|---|
| 9 | C$_2$H$_5$NH | CH(CH$_3$)C$_2$H$_5$ | O | $n_D^{20} = 1.4315$ |
| 10 | C$_2$H$_5$O | n-C$_3$H$_7$ | S | |
| 11 | C$_2$H$_5$O | CH(CH$_3$)C$_2$H$_5$ | S | |
| 12 | C$_2$H$_5$NH | n-C$_3$H$_7$ | S | |
| 13 | C$_2$H$_5$NH | CH(CH$_3$)C$_2$H$_5$ | S | |

EXAMPLE 14 (Starting substances of the formula III)

Step 1

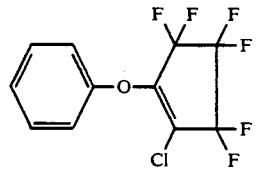

This is prepared as described by: R. Stockel, Can. J. Chem., 53, 2302 (1975)

Step 2

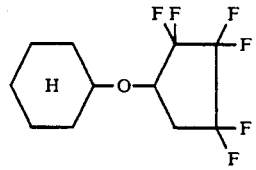

In a 1.3 l autoclave, 605 g (2 mol) of 2-chloro-3,3,4,4,5,5-hexafluorocyclopentenyl phenyl ether (from Step 1) are suspended in 500 ml of pH 9 buffer (bora/HCl), and the mixture is hydrogenated at 70°–80° C. with 80 bar hydrogen, using 50 g of palladium/charcoal. The catalyst is filtered off, and the filtrate is extracted with dichloromethane. Distillation gives 2,2,3,3,4,4-hexafluorocyclopentyl cyclohexyl ether.

B.p.: 86°–89° C.

Yield: 502 g (91% of theory)

$^1$H-NMR: 1.08–1.54 ppm (m, 6H); 1.83 ppm (m, 4H); 2.34 ppm (m, 1H); 2.71 ppm (m, 1H); 3.48 ppm, (m, 1H); 4.20 ppm (m, 1H)

$^{19}$F-NMR (against CF$_3$COOH): −33.5 ppm (m, 2F); −47.3 ppm (m, 2F); −55.0 ppm (m, 2F)

The alkali metal salts can be obtained from the alcohol by the generally customary salt formation methods.

Step 3

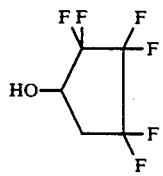

276 g (1 mol) of 2,2,3,3,4,4-hexafluorocyclopentyl cyclohexyl ether from Step 2 are added dropwise to 300 ml of concentrated sulphuric acid until the evolution of gas has ceased, and the cleavage product is distilled off at 130°–140° C. The mixture of the desired alcohol and cyclohexene is redistilled. In this manner, distillation gives 2,2,3,3,4,4-hexafluorocyclopentanol.

Yield: 165 g (85% of theory)
B.p.: 130°–132° C.

$^1$H-NMR: 2.39 ppm (m, 1H); 2.72 ppm (m, 1H); 3.27 ppm (s, 1H); 4.38 ppm (m, 1H)

$^{19}$F-NMR: (against CF$_3$COOH): −32.2 ppm (m, 2F); −49.7 ppm, (m, 2F); −54.2 ppm (m, 2F)

The biological action of the compounds according to the invention will be illustrated with the aid of the following examples.

EXAMPLE A

Phaedon Larvae Test

Solvent: 3 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*) while the leaves are still moist.

After the specified periods of time, the destruction in % is determined. 100% means that all the beetle larvae have been killed; 0% means that none of the beetle larvae have been killed.

In this test, for example the compounds of Preparation Examples 1, 5, 6 and 7 showed a destruction of 100% after 3 days, at an exemplary active compound concentration of 0.01%.

EXAMPLE B

Critical Concentration Test/Soil Insects

Test insect: *Diabrotica balteata* larvae in the soil
Solvent: 4 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm (mg/l), being appropriate. The soil is transferred into 0.5 l pots and the pots are left to stand at 20° C.

Immediately after the test has been set up, 5 pregerminated maize kernels are placed into each pot. After 1 day, the test insects in question are introduced into the treated soil. After a further 7 days, the degree of effectiveness of the active compound is determined in % by counting the dead and live test insects. The degree of effectiveness is 100% if all the test insects have been killed and is 0% if just as many test insects are still alive as in the case of the untreated control.

In this test, for example the compound of Preparation Example 6 showed a degree of effectiveness of 100% at an exemplary concentration of 20 ppm.

EXAMPLE C

Critical Concentration Test/Soil Insects

Test insect: *Phorbia antiqua* larvae in the soil
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm (=mg/l), being decisive. The treated soil is transferred into pots and the pots are left to stand at room temperature.

After 24 hours, the test insects are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, for example the compounds of Preparation Examples 4 and 6 showed a destruction number of 100% at an exemplary concentration of 20 ppm.

EXAMPLE D

Critical Concentration Test/Nematodes

Test nematode: *Meloidogyne incognita*
Solvent: 4 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil which is heavily infested with the test nematodes. The concentration of the active compound in the preparation is of practically no importance here, only the amount of active compound per unit volume of soil, which is given in ppm, being decisive. The treated soil is transferred into pots, lettuce is sown in and the pots are kept at a greenhouse temperature of 25° C.

After four weeks, the lettuce roots are examined for infestation with nematodes (root galls), and the degree of effectiveness of the active compound is determined in %. The degree of effectiveness is 100% if infestation is avoided completely and is 0% when the infestation is just as high as in the control plants in untreated, but equally infested soil.

In this test, for example the compound of Preparation Example 6 showed a degree of effectiveness of 100% at an exemplary concentration of 10 ppm.

EXAMPLE E

Critical Concentration Test

Test nematode: *Globodera rostochiensis*
Solvent: 4 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil which is heavily infested with the test nematodes. The concentration of the active compound in the preparation is of practically no importance here, only the amount of active compound per unit volume of soil, which is given in ppm, being decisive. The treated soil is transferred into pots, potatoes are planted in and the pots are kept at a greenhouse temperature of 20° C.

After six weeks, the potato roots are examined for cysts, and the degree of effectiveness of the active compound is determined in %. The degree of effectiveness is 100% if infestation is avoided completely and is 0% if the level of infestation is just as high as in the control plants in untreated, but equally infested, soil.

In this test, for example the compound of Preparation Example 6 showed a degree of effectiveness of 100% at an exemplary concentration of 10 ppm.

EXAMPLE F

Seed Treatment Test/Soil Insects

Test insect: *Diabrotica balteata* larvae in the soil
Test plant: *Zea mays*
Solvent: 1 part by weight of acetone
Carrier material: kaolin To prepare a suitable preparation of active compound, the active compound is dissolved in acetone, and 1 part by weight of active compound/acetone is mixed with 5 parts by weight of kaolin. This active compound preparation is used for treating maize seed at the required application rates. The maize is sown in 0.5 l pots with standardised soil, at 20° C. room temperature.

After 1 day, approx. 30 Diabrotica larvae are introduced into each pot. After a further 7 days, the degree of effectiveness of the active compound is determined in % by counting the dead and live test insects. The degree of effectiveness is 100% if all test insects have been killed and is 0% if just as many test insects are alive as in the untreated control.

In this test, for example the compound of Preparation Example 6 showed a degree of effectiveness of 100% at an exemplary application rate of 2 g per kg of seed.

EXAMPLE G

Seed Treatment Test/Soil Insects

Test insect: *Phorbia antiqua* grubs in the soil
Test plant: *Allium cepa*
Solvent: 1 part by weight of acetone
Carrier material: kaolin To prepare a suitable preparation of active compound, the active compound is dissolved in acetone, and 1 part by weight of active compound/acetone is mixed with 5 parts by weight of kaolin. This active compound preparation is for treating the onion seed at the required application rates. The seed is sown in 0.5 l pots with standardised soil, at 20° C. greenhouse temperature. After the onions have emerged, they are infected artificially with onion fly eggs. The test is evaluated after 14 days. The degree of effectiveness is 100% when all onion plants show good growth and 0% when all test plants (as in the untreated control) have been destroyed.

In this test, for example the compound of Preparation Example 6 showed a degree of effectiveness of 100% at an exemplary application rate of 2 g per kg of seed.

EXAMPLE H

Fly Test

Test animals: *Musca domestica*, strain WHO(N)
Solvent:
  35 parts by weight of ethylene glycol monoethyl ether
  35 parts by weight of nonylphenol polyglycol ether To prepare a suitable formulation, three parts by weight of active compound are mixed with seven parts of the abovementioned solvent/emulsifier mixture, and the resulting emulsion concentrate is diluted with water to the particular desired concentration.

2 ml of this active compound preparation are pipetted onto filter paper discs ($\phi$9.5 cm) which are in Petri dishes of a corresponding size. When the discs are dry, 25 test insects are introduced into the Petri dishes and covered.

After 6 hours, the effectiveness of the active compound preparation is determined. The effectiveness is expressed in %. 100% means that all flies have been killed; 0% means that no flies have been killed.

In this test, for example the compounds of Preparation Examples 1, 5 and 7 showed an effectiveness of 100% at an exemplary active compound concentration of 1,000 ppm.

EXAMPLE J

Cockroach Test

Test insects: *Periplaneta americana*
Solvent:
  35 parts by weight of ethylene glycol monomethyl ether
  35 parts by weight of nonylphenol polyglycol ether To prepare a suitable formulation, three parts by weight of active compound are mixed with seven parts of the abovementioned solvent/emulsifier mixture, and the resulting emulsion concentrate is diluted with water to the particular desired concentration.

2 ml of this active compound preparation are pipetted onto filter paper discs ($\phi$9.5 cm) which are in the Petri dishes of a corresponding size. When the discs are dry, 5 test insects are introduced and covered.

After 3 days, the effectiveness of the active compound preparation is determined. The effectiveness is expressed in %. 100% means that all cockroaches have been killed; 0% means that no cockroaches have been killed.

In this test, for example the compounds of Preparation Examples 1 and 7 showed an effectiveness of 100% at an exemplary active compound concentration of 1,000 ppm.

EXAMPLE K

Blowfly Larvae Test

Test animals: *Lucilia cuprina* larvae
Emulsifier:
  35 parts by weight of ethylene glycol monomethyl ether
  35 parts by weight of nonylphenol polyglycolether To prepare a suitable preparation of active compound, three parts by weight of active compound are mixed with seven parts by weight of the abovementioned mixture, and the resulting emulsion concentrate is diluted with water to the particular desired concentration.

Approximately 20 resistant *Lucilia cuprina* larvae are introduced into a test tube which contains approx. 1 cm$^3$ of horse meat and 0.5 ml of the active compound preparation. After 24 hours, the effectiveness of the active compound preparation is determined. 100% means that all blowfly larvae have been killed.

In this test, for example the compounds of Preparation Examples 1, 4, 5 and 7 showed an action of 100% at an exemplary active compound concentration of 1,000 ppm.

EXAMPLE L

Grain Weevil Test

Test insects: *Sitophilus granarius*
Solvent:
  35 parts by weight of ethylene glycol monomethyl ether
  35 parts by weight of nonylphenol polyglycol ether To prepare a suitable formulation, three parts by weight of active compound are mixed with seven parts of the abovementioned solvent/emulsifier mixture, and the resulting emulsion concentrate is diluted with water to the particular desired concentration.

2 ml of this active compound preparation are pipetted onto filter paper discs ($\phi$9.5 cm) which are in Petri dishes of a corresponding size. After the discs have dried, 30 test insects of S. granarius are introduced into the Petri dishes and covered.

After 3 days, the effectiveness of the active compound preparation is determined. The effectiveness is expressed in %. 100% means that all grain weevils have been killed; 0% means that no grain weevils have been killed.

In this test, for example the compounds of Preparation Examples 1 and 7 showed an action of 100% at an exemplary active compound concentration of 1,000 ppm.

We claim:

1. A O-halogenocyclopentyl S-alkyl (di) thiophosphoric(phosphonic) acid ester derivative of the general formula (I)

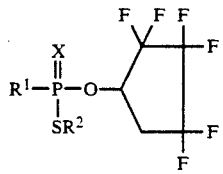

(I)

in which $R^1$ represents alkyl, alkoxy or the radical

where
$R^3$ represents hydrogen or alkyl and
$R^4$ represents hydrogen, alkyl, —COH (formyl) or optionally halogen-substituted —CO-alkyl (acyl),
$R^2$ represents alkyl or alkoxyalkyl and
X represents oxygen or sulphur.

2. A compound according to claim 1, in which
$R^1$ represents $C_1$-$C_6$-alkyl, $C_1$-$C_6$-alkoxy or —NR$^3$R$^4$ where
  $R^3$ represents hydrogen or $C_1$-$C_6$-alkyl and
  $R^4$ represents hydrogen, $C_1$-$C_6$-alkyl, HCO— (formyl) or optionally halogen-substituted —CO—$C_1$-$C_4$-alkyl (acyl),
$R^2$ represents $C_1$-$C_6$-alkyl or $C_1$-$C_6$-alkoxy-$C_1$-$C_6$-alkyl and
X represents oxygen or sulphur.

3. A compound according to claim 1, in which
$R^1$ represents $C_1$-$C_4$-alkyl, $C_1$-$C_4$-alkoxy or —NR$^3$R$^4$ where
  $R^3$ represents hydrogen or $C_1$-$C_4$-alkyl and
  $R^4$ represents hydrogen, $C_1$-$C_4$-alkyl, HCO— or optionally halogen-substituted —CO—$C_1$-$C_4$-alkyl,
$R^2$ represents $C_1$-$C_4$-alkyl or $C_1$-$C_4$-alkoxy-$C_1$-$C_4$-alkyl and
X represents oxygen or sulphur.

4. A compound according to claim 1, in which
$R^1$ represents $C_1$-$C_3$-alkyl, methoxy, ethoxy, —NHCH$_3$ or —NHC$_2$H$_5$,
$R^2$ represents $C_3$-$C_4$-alkyl and
X represents oxygen or sulphur.

5. A compound according to claim 1, where X represents oxygen.

6. An insecticidal, acaricidal or nematicidal composition comprising an insecticidally, acaricidally or nematicidally effective amount of a compound according to claim 1 and a diluent.

7. A method of combating insects, acarids or nematodes which comprises applying to such insects, acarids or nematodes an insecticidally, acaricidally or nematicidally effective amount of a compound according to claim 1.

8. A compound of the formula (XVIII)

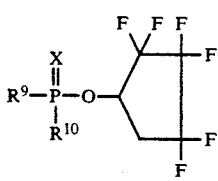

(XVIII)

in which
  (a) $R^9$ has the meaning of $R^1$ and $R^{10}$ represents halogen or SZ$^1$ or
  (b) $R^9$ represents halogen and $R^{10}$ represents SR$^2$,
  where $R^1$ and $R^2$ have the meaning given in claim 1, and
  $Z^1$ represents an equivalent of an alkali metal ion.

* * * * *

UNITED STATES PATENT AND TRADEMARK OFFICE
CERTIFICATE OF CORRECTION

PATENT NO. : 5,164,383
DATED : November 17, 1992
INVENTOR(S) : Kruger et al

It is certified that error appears in the above-indentified patent and that said Letters Patent is hereby corrected as shown below:

Title page, Item [54] and Column 1, lines 1-4, should read as follows:
--O-(2,2,3,3,4,4-HEXAFLUOROCYCLOPENTYL)-S-ALKYL (DI) THIOPHOSPHORIC ACID ESTER DERIVATIVES AND PROCESS OF USE AS PESTICIDES--

Abstract, line 1, delete "(di) thiphosphoric(-" and substitute --(di) thiophosphoric(- --

Abstract, line 6 after " 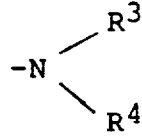 "

insert --where--

Signed and Sealed this

Twenty-first Day of June, 1994

*Attest:*

BRUCE LEHMAN

*Attesting Officer*   Commissioner of Patents and Trademarks